(12) United States Patent
Limma

(10) Patent No.: US 9,707,130 B2
(45) Date of Patent: Jul. 18, 2017

(54) PROTECTIVE EYESHIELDS AND METHOD OF USE

(71) Applicant: Lori Ann Limma, Florham Park, NJ (US)

(72) Inventor: Lori Ann Limma, Florham Park, NJ (US)

( * ) Notice: Subject to any disclaimer, the term of this patent is extended or adjusted under 35 U.S.C. 154(b) by 55 days.

(21) Appl. No.: 14/827,516

(22) Filed: Aug. 17, 2015

(65) Prior Publication Data

US 2017/0049625 A1    Feb. 23, 2017

(51) Int. Cl.
    *A61F 9/02*      (2006.01)
    *G02C 5/12*      (2006.01)
    *G02C 1/00*      (2006.01)
    *G02C 3/00*      (2006.01)
    *G02C 11/00*     (2006.01)

(52) U.S. Cl.
CPC ............... *A61F 9/026* (2013.01); *A61F 9/02* (2013.01); *A61F 2009/021* (2013.01); *G02C 1/00* (2013.01); *G02C 3/00* (2013.01); *G02C 3/003* (2013.01); *G02C 5/12* (2013.01); *G02C 5/122* (2013.01); *G02C 5/124* (2013.01); *G02C 5/126* (2013.01); *G02C 11/00* (2013.01)

(58) Field of Classification Search
CPC . G02C 11/00; G02C 1/00; G02C 3/00; G02C 3/003; G02C 5/12; G02C 5/122; G02C 5/124; G02C 5/126; A61F 9/02; A61F 2009/021
USPC ...... 351/41, 87, 88, 70, 71, 76, 78, 79, 131, 351/132, 136, 155; 2/9, 15, 426, 431, 2/439, 440, 442
See application file for complete search history.

(56) References Cited

U.S. PATENT DOCUMENTS

| | | | | |
|---|---|---|---|---|
| 1,942,393 | A | * 1/1934 | Baker | G02C 5/045 351/128 |
| 3,758,202 | A | 9/1973 | Chunga, Sr. | |
| 3,832,043 | A | 8/1974 | Usdan | |
| 3,955,885 | A | 5/1976 | Aronsohn | |
| 4,790,031 | A | 12/1988 | Duerer | |
| 4,792,222 | A | * 12/1988 | Labenz | G02C 5/122 351/136 |
| 5,159,359 | A | * 10/1992 | Pauly | G02C 5/124 351/124 |
| 5,291,230 | A | * 3/1994 | Bradley | G02C 5/122 351/128 |
| 5,459,882 | A | 10/1995 | Yamamoto | |

(Continued)

*Primary Examiner* — William R Alexander
(74) *Attorney, Agent, or Firm* — Thomas J. Germinario

(57) ABSTRACT

Protective eyeshields have two lenses, which are interconnected at their proximal ends by an adjustable nose-bridge and are releasably connectable at their distal ends by two conjugate connecting straps. The lenses have a longitudinal convex curvature so that they follow the contours of the wearer's face. They are substantially trapezoidal in shape, tapering from the proximal end to the distal end. The lenses are made of a light-weight semi-rigid plastic, such as plexiglass, and may be clear transparent or tinted. Plastic foam padding is provided along the longitudinal edges of the lenses to cushion the area of contact between the lenses and the wearer's face. The weight of the lenses is support from below by four support struts, two of which are nose supports and two which are cheek supports. Each of the support struts integrally comprises a stem element and a contact pad element.

4 Claims, 2 Drawing Sheets

(56) References Cited

U.S. PATENT DOCUMENTS

| | | | | |
|---|---|---|---|---|
| 5,506,638 A | | 4/1996 | Donner | |
| 5,583,586 A | * | 12/1996 | Evans | G02C 3/003 |
| | | | | 351/130 |
| 5,790,230 A | * | 8/1998 | Sved | A61F 9/025 |
| | | | | 351/110 |
| 6,247,811 B1 | * | 6/2001 | Rhoades | A61F 9/026 |
| | | | | 2/431 |
| 6,976,756 B1 | * | 12/2005 | Chen | G02C 5/126 |
| | | | | 351/136 |
| 7,472,991 B1 | * | 1/2009 | Chen | G02C 5/122 |
| | | | | 351/137 |
| 2001/0055093 A1 | * | 12/2001 | Saitoh | G02C 5/124 |
| | | | | 351/136 |
| 2004/0066486 A1 | * | 4/2004 | Yi | G02C 11/08 |
| | | | | 351/79 |
| 2004/0130675 A1 | * | 7/2004 | Einarsson | G02C 9/00 |
| | | | | 351/128 |
| 2004/0187196 A1 | | 9/2004 | Haslbeck | |
| 2006/0082723 A1 | * | 4/2006 | Jamie | G02C 3/003 |
| | | | | 351/123 |
| 2010/0122398 A1 | | 5/2010 | Luciano | |
| 2013/0196284 A1 | * | 8/2013 | Brawn | A61C 7/00 |
| | | | | 433/24 |
| 2013/0278885 A1 | * | 10/2013 | Hasky | G02C 3/003 |
| | | | | 351/155 |
| 2013/0298318 A1 | * | 11/2013 | Rogers | A42B 3/185 |
| | | | | 2/439 |
| 2015/0000017 A1 | | 1/2015 | Lee | |
| 2015/0338658 A1 | * | 11/2015 | Davis | G02B 27/0172 |
| | | | | 345/8 |
| 2016/0262922 A1 | * | 9/2016 | Portney | A61F 5/01 |

\* cited by examiner

PROTECTIVE EYESHIELDS AND METHOD OF USE

FIELD OF INVENTION

The present invention relates generally to the field of eyeglasses and eyeshields, and more particularly to eyeshields designed to protect the wearer's eyes during sleep.

BACKGROUND OF THE INVENTION

In certain circumstances, it is necessary to protect a person's eyes during sleep, when the eyes might otherwise be rubbed by the sleeper or come into contact with bedding. Circumstances warranting such protection may include post-operative recovery from eye surgery or cosmetic eye enhancements, such as eyelash extensions.

Unless properly designed, however, eyeshields will tend to move and shift position on the wearer's face as he/she sleeps, causing discomfort and potentially impacting sensitive eye areas. In this regard, it's particularly important to prevent the lenses of the eyeshield from being pushed back against the eyes by pressure from contact with bedding or the wearer's body.

SUMMARY OF THE INVENTION

The protective eyeshields of the present invention comprise two lenses, which are interconnected at their proximal ends by an adjustable nose-bridge and are releasably connectable at their distal ends by two conjugate connecting straps. The releasable connection between the connecting straps can be provided by one or more hook-and-loop connectors or one or more snap or catch connectors.

The lenses have a longitudinal convex curvature so that they follow the contours of the wearer's face. They are substantially trapezoidal in shape, tapering from the proximal end to the distal end. The lenses are made of a light-weight semi-rigid plastic, such as plexi-glass, and may be clear transparent or tinted. Optionally, the lenses may have a prescription or non-prescription corrective curvature.

Plastic foam padding is provided along the longitudinal edges of the lenses to cushion the area of contact between the lenses and the wearer's face. The weight of the lenses is supported from below by four support struts, two of which are nose supports and two which are cheek supports. Each of the support struts integrally comprises a stem element and a contact pad element.

The support struts are made of a shape-retaining malleable plastic, metal or plastic-metal combination, such as a malleable wire core encased in flexible plastic. The support strut material is manually deformable at room temperature to enable shape-retaining bending of the stem element and shape-retaining angular rotation of the contact pad element. By "shape-retaining," it is meant that the material is able to retain a deformed shape after removal of the deforming force. The support struts are malleably adaptable to the facial configuration of the wearer so as to provide effective weight-bearing engagement between the contact pad elements of the cheek supports and the wearer's cheek bones and between the contact pad elements of the nose supports and the wearer's nose.

The adjustable nose-bridge which interconnects the two lenses can have a mating notch-and-groove configuration, such as that disclosed in U.S. Pat. No. 5,459,882, the disclosure of which is incorporated herein by reference, or a closed-loop configuration, such as that disclosed in U.S. patent publication 2004/0187196, the disclosure of which is also incorporated herein by reference.

In use, the wearer aligns the lenses with his/her eyes, fastens the connecting straps, bends the stems elements and rotates the contact pad elements of the two nose supports so as to bring these contact pad elements into flush engagement with the wearer's nose, and then bends the stem elements and rotates the contact pad elements of the cheek supports so as to bring these contact pad elements into flush engagement with the wearer's cheeks.

The foregoing summarizes the general design features of the present invention. In the following sections, specific embodiments of the present invention will be described in some detail. These specific embodiments are intended to demonstrate the feasibility of implementing the present invention in accordance with the general design features discussed above. Therefore, the detailed descriptions of these embodiments are offered for illustrative and exemplary purposes only, and they are not intended to limit the scope either of the foregoing summary description or of the claims which follow.

DETAILED DESCRIPTION OF THE PREFERRED EMBODIMENT

Figure 1:
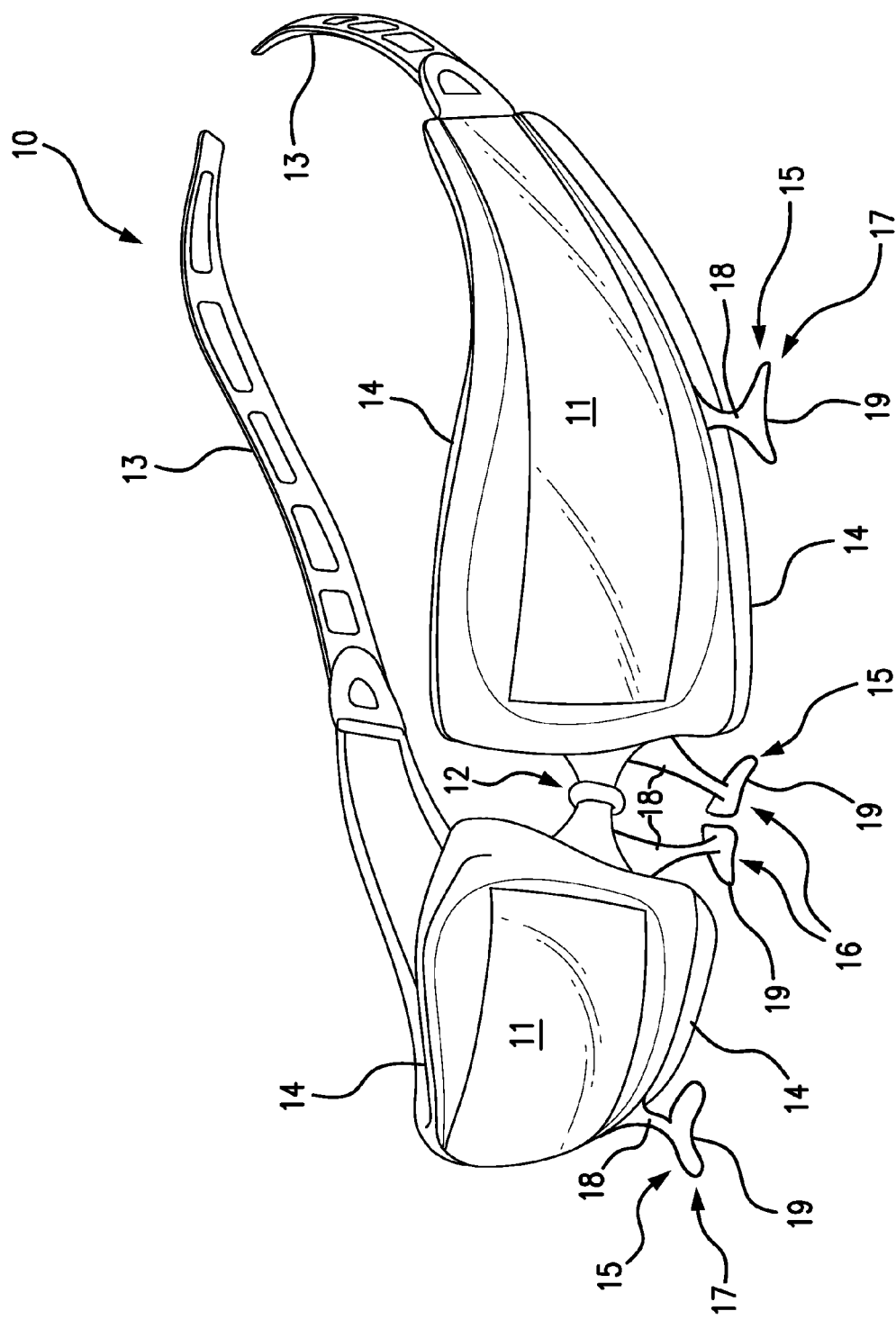
FIG. 1 is a perspective view of one embodiment of the protective eyeshields of the present invention.

Referring to FIG. 1, one embodiment of the protective eyeshields of the present invention 10 comprises two lenses 11, which are interconnected at their proximal ends by an adjustable nose-bridge 12. The lenses 11 are releasably connectible at their distal ends by two conjugate connecting straps 13. The releasable connection between the connecting straps can be provided by one or more hook-and-loop connectors or one or more snap or catch connectors, such as are well known in the art.

The lenses 11 have a longitudinal convex curvature so that they follow the contours of the wearer's face. They are substantially trapezoidal in shape, tapering from the proximal end to the distal end. The lenses 11 are made of a light-weight semi-rigid plastic, such as plexi-glass, and may be clear transparent or tinted. Optionally, the lenses 11 may have a prescription or non-prescription curvature to correct the wearer's vision.

Plastic foam padding 14 is provided along the longitudinal edges of the lenses 11 to cushion the area of contact between the lenses 11 and the wearer's face. The weight of the lenses 11 is supported from below by four support struts 15, two of which are nose supports 16 and two which are cheek supports 17. Each of the support struts 15 integrally comprises a stem element 18 and a contact pad element 19.

The support struts 15 are made of a shape-retaining malleable plastic, metal or plastic-metal combination, such as a malleable wire core encased in flexible plastic. The support strut material is manually deformable at room temperature to enable shape-retaining bending of the stem element 18 and shape-retaining angular rotation of the contact pad element 19. The support struts 15 are malleably adaptable to the facial configuration of the wearer so as to provide effective weight-bearing engagement between the contact pad elements 19 of the cheek supports 17 and the wearer's cheek bones and between the contact pad elements 19 of the nose supports 16 and the wearer's nose.

The adjustable nose-bridge 12 which interconnects the two lenses 11 can have a mating notch-and-groove configuration, or a closed-loop configuration.

In use, the wearer aligns the lenses 11 with his/her eyes, fastens the connecting straps 13, bends the stem elements 18 and rotates the contact pad elements 19 of the two nose supports 16 so as to bring these contact pad elements 19 into flush engagement with the wearer's nose, and then bends the stem elements 18 and rotates the contact pad elements 19 of the cheek supports 17 so as to bring these contact pad elements 19 into flush engagement with the wearer's cheeks.

Figure 2A:
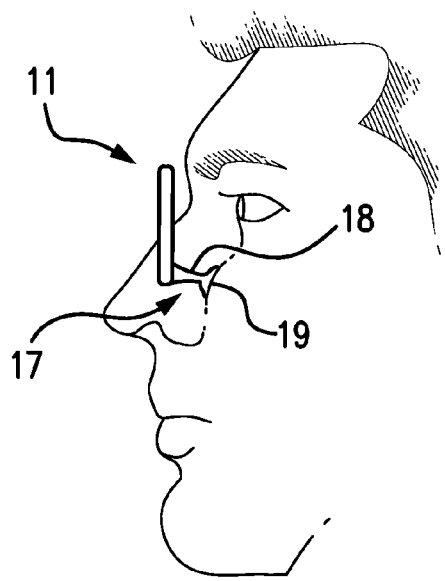
FIGS. 2A-2C are three partial side-profile views of the protective eyeshields worn on three different faces, with the cheek supports adjusted so that their contact pad elements are in flush engagement with the wearer's cheek bones.
Figure 2B:
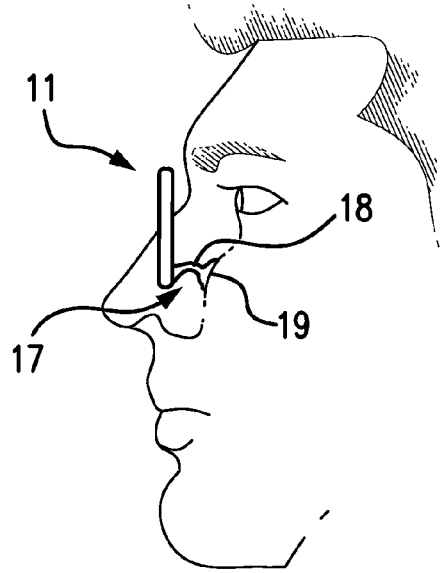
Figure 2C:
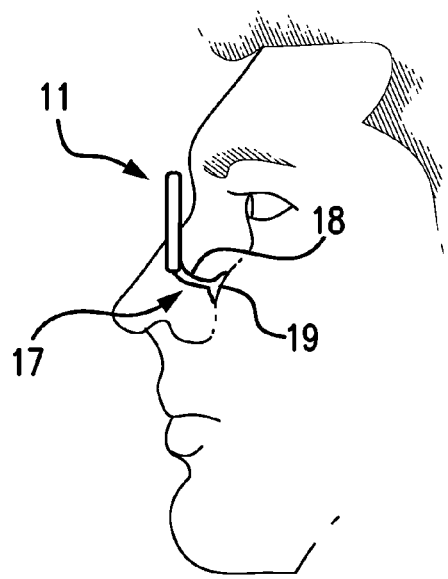

FIGS. 2A-2C are exemplary illustrations of adjustments of the cheek supports 17 to adapt to three different facial configurations: non-prominent cheekbones (FIG. 2A), high prominent cheekbones (FIG. 2B), and low prominent cheekbones (FIG. 2C). In FIG. 2A, the stem element 18 extends substantially unbent, with the contact pad element 19 substantially perpendicular to the stem element 18, so as to engage flush with the cheekbone. In FIG. 2B, the stem element 18 is given a concave (inward) bend, with the contact pad element 19 at an acute angle relative to the stem element 18, so as to engage flush with the high cheekbone. In FIG. 2C, the stem element 18 is given a convex (outward) bend, with the contact pad element 19 at an obtuse angle relative to the stem element 18, so as to engage flush with the low cheek bone.

Although the preferred embodiment of the present invention has been disclosed for illustrative purposes, those skilled in the art will appreciate that many additions, modifications and substitutions are possible, without departing from the scope and spirit of the present invention as defined by the accompanying claims.

What is claimed is:

1. Protective eyeshields comprising:
   two lenses, each having a proximal end, a distal end and two longitudinal edges, which consist of a top longitudinal edge and a bottom longitudinal edge, wherein the two lenses are interconnected at the proximal ends of the lenses by an adjustable nose-bridge, and wherein the two lenses are releasably connected at the distal ends of the lenses by two conjugate connecting straps extending from the distal ends of the lenses, and wherein the two longitudinal edges of each lens have plastic foam padding that is adapted and configured to cushion an area of facial contact; and
   four support struts, consisting of two cheek support struts, one of which extends from the bottom longitudinal edge of each lens, and two nose support struts, one of which extends from the proximal end of each lens, wherein each support strut integrally comprises a stem element and a contact pad element, and wherein each support strut is made of a shape-retaining malleable material that is manually deformable at room temperature and enables shape-retaining bending of the stem element and shape-retaining angular rotation of the contact pad element, and wherein the shape-retaining malleable material retains a deformed shape after removal of a deforming force.

2. The protective eyeshields of claim 1, wherein each of the lenses has a longitudinal convex curvature, adapted to a facial contour.

3. The protective eyeshields of claim 2, wherein each of the lenses is substantially trapezoidal in shape and tapers from the proximal end to the distal end.

4. A method of using protective eyeshields, comprising the following steps:
   (a) providing the protective eyeshields, comprising two lenses, each having a proximal end, a distal end and two longitudinal edges, which consist of a top longitudinal edge and a bottom longitudinal edge, wherein the two lenses are interconnected at the proximal ends of the lenses by an adjustable nose-bridge, and wherein the two lenses are releasably connected at the distal ends of the lenses by two conjugate connecting straps extending from the distal ends of the lenses, and wherein the two longitudinal edges of each lens have plastic foam padding that is adapted and configured to cushion an area of facial contact; and the protective eyeshield further comprise four support struts, consisting of two cheek support struts, one of which extends from the bottom longitudinal edge of each lens, and two nose support struts, one of which extends from the proximal end of each lens, wherein each support strut integrally comprises a stem element and a contact pad element, and wherein each support strut is made of a shape-retaining malleable material that is manually deformable at room temperature and enables shape-retaining bending of the stem element and shape-retaining angular rotation of the contact pad element, and wherein the shape-retaining malleable material retains a deformed shape after removal of a deforming force;
   (b) aligning the two lenses at an eye level;
   (c) fastening the connecting straps together;
   (d) bending the stem elements of the two nose support struts so that the contact pad elements of the two nose support struts engage both sides of a wearer's nose;
   (e) rotating the contact pad elements of the two nose support struts so that the contact pad elements of the two nose support struts come into flush engagement with both sides of the wearer's nose;
   (f) bending the stem elements of the two cheek support struts so that the contact pad elements of the two cheek support struts engage both of the wearer's cheeks; and
   (g) rotating the contact pad elements of the two cheek support struts so that the contact pad elements of the two cheek support struts come into flush engagement with both of the wearer's cheeks.

* * * * *